United States Patent [19]

Silvestrini

[11] Patent Number: 4,621,638
[45] Date of Patent: Nov. 11, 1986

[54] HARD ELASTIC SUTURES

[75] Inventor: Thomas A. Silvestrini, East Lyme, Conn.

[73] Assignee: Pfizer Hospital Products Group, Inc., New York, N.Y.

[21] Appl. No.: 754,716

[22] Filed: Jul. 15, 1985

Related U.S. Application Data

[63] Continuation-in-part of Ser. No. 635,790, Jul. 30, 1984, abandoned.

[51] Int. Cl.⁴ .............................................. A61B 17/00
[52] U.S. Cl. ............................... 128/335.5; 264/176.F 264/178 F
[58] Field of Search ................. 128/335.5; 264/176 F, 264/178 F

[56] References Cited

U.S. PATENT DOCUMENTS

| | | | |
|---|---|---|---|
| 3,359,983 | 12/1967 | Northey | 128/335.5 |
| 3,454,011 | 7/1969 | Wagner | 128/335.5 |
| 3,565,077 | 2/1971 | Glick | 128/335.5 |
| 3,630,205 | 12/1971 | Listner | 128/335.5 |

Primary Examiner—Jacqueline V. Howard
Attorney, Agent, or Firm—Charles J. Knuth; Peter C. Richardson; Gezina Holtrust

[57] ABSTRACT

A surgical suture made of a polymer filament having the "hard" elastic properties of reversible elasticity and retention of diameter on stretching.

20 Claims, 3 Drawing Figures

HARD ELASTIC SUTURES

CROSS-REFERENCE TO RELATED APPLICATIONS

This application is a continuation-in-part of application Ser. No. 635,790, filed July 30, 1984, now abandoned.

BACKGROUND OF THE INVENTION

This invention relates to the field of surgical sutures, more particularly to the field of fine sutures for corneal surgery.

Opthalmic sutures are necessarily of fine gauge, and so must be made of strong filaments. However, if the suture is too fine, even though strong, the suture can cut through and damage the corneal tissue. If too large, the suture will not allow burying the suture knot in the sclera and results in irritation and discomfort. Conventional ophthalmic sutures are generally made of nylon filaments. These materials produce sutures that perform reasonably well, but still have deficiencies. In particular, they are not elastic enough to expand and contract adequately with tissue swelling due to edema. This can result in damage and poor wound healing. Therefore, it would be advantageous to have an elastic opthalmic suture. However, most elastic filaments shrink in diameter as they elongate. This makes them unsuitable for use as opthalmic sutures because, as the wound swells and tension in the suture increases, the suture diameter decreases. This reduced diameter coupled with the increased tension make it more likely that the suture will cut through and damage the delicate tissue.

Thus, the ideal suture for corneal tissue would be of high strength to allow use of fine size, reversibly elastic to accommodate edema, and capable of substantially maintaining its initial diameter when elongated to minimize cutting through tissue.

U.S. Pat. No. 3,630,205 discloses flexible polypropylene sutures. However, the polypropylene used is not a "hard" elastic material as defined hereafter.

SUMMARY OF THE INVENTION

According to the invention, a suture is made of hard elastic filaments of a body-compatible polymer.

The term "hard elastic" is used by R. G. Quinn et al., J. Macromol. Sci. Phys., B5(4), 721–738 (Dec., 1971) with reference to fibers prepared from semicrystalline polymers having long range mechanical elasticity, i.e. a high degree of length recovery from large extensions, specifically at least about 90% recovery on 30% extension, a marked reduction in apparent density on stretching, and generation of very large amounts of accessible volume and surface area on stretching. The large, mainly reversible reduction in apparent density on stretching sharply distinguishes the hard elastic filament from elastic filaments. This reduction in density results in little or no decrease in filament diameter on stretching.

In accordance with the invention, a hard elastic filament is one which (1) shows substantially less decrease in filament diameter on stretching when compared to conventional elastomeric filament, (2) is at least about 90% reversibly elastic on elongation of up to 30% subsequent to one elongation and relaxation cycle, and (3) exhibits characteristic elasticity in which the slope of the stress strain curve of the filament changes without plastic yield deformation.

As to (2) above, the 90% reversible elasticity on 30% elongation is found in elongation and relaxation cycles subsequent to the first elongation and relaxation cycle.

The hard elastic filament according to the invention is made from a polymer having a special crystalline morphology which is a result of specific high stress spinning conditions described in the art cited hereafter.

Polymers capable of forming hard elastic filaments under high stress spinning conditions are polyolefins such as isotactic polybutylene (also known as poly(butene-1)), isotatic polypropylene(PP) and polyethylene(PE), and mixtures of isotactic and non-isotactic polyolefins.

Isotactic copolymers of olefins such as butene-1/ethylene copolymers and blends of isotactic homo- and copolymers of olefins such as PP/PE blends are suitable as well. Examples of other suitable polymers are polyoxymethylene, polyisobutylene oxide, polyester and nylon. All of the above polymers are suitable for use as nonabsorbable sutures.

Other suitable polymers are polycaprolactone, polycaprolactam, polyhydroxybutyric acid(PHB), polyglycolic acid(PGA) and polylactic acid(PLA), and blends thereof such as blends of PGA and PLA, and PHB and PGA. These polymers are slowly absorbable in the body and may therefore be made into absorbable sutures.

The manufacture of hard elastic filaments is described in the art, for instance in U.S. Pat. Nos. 4,006,208 (polyisobutylene oxide), 3,840,510 (butene-1 polymers), 3,686,385 (poly(butene-1)), 3,549,743 (PP), 3,513,110 (polyester and polycarbonamide), 3,432,590 (PP), 3,323,190 (PP), 3,330,897 (polyolefines) and 3,256,258 (PP), the disclosures of which patents are herewith incorporated by reference.

Fine gauge sutures can be made of hard elastic filaments in either monofilament or multifilament form. While fine gauge hard elastic monofilament sutures are especially suitable for opthalmic use, larger diameter monofilament and multifilament sutures are useful in general surgery.

It is the purpose of this invention to provide a suture which is reversibly elastic to stretch on wound swelling, but does not significantly decrease in diameter during that elongation. It is another purpose to provide such a suture as a fine gauge monofilament suitable for opthalmic use.

DESCRIPTION OF THE PREFERRED EMBODIMENTS

Continuous filaments with hard elastic properties can be made from a number of highly crystalline polymers that are also suitable for use as sutures in the human body, as described above. Filaments made of polybutylene and PP/PE blends are advantageous since hard elastic properties are reliably obtained on proper processing of these polymers. Isotactic PP is advantageously used because of combination of high strength and good eye-compatibility. A suitable grade of crystalline isotactic PP is sold by Hercules Inc. under the trademark "Profax". Shell Polybutylene 4110, 0400, 0300, 0200, 8640, 8240 and 8010 are suitable butylene and butylene-ethylene polymers available from Shell Chemical Company. Exxon polypropylene (DMF #492) is a suitable mixture of isotactic and non-isotactic polypropylene available from the Exxon Corporation.

A conventional elastomeric filament has a constant density and volume during stretching so that the diameter of the filament must decrease during stretching. Such decrease can be accurately calculated. The results of such calculations are set out in FIG. 3 and below as follows:

| % Elongation | % Decrease in Diameter |
| --- | --- |
| 0 | 0 |
| 10 | 4.7 |
| 20 | 8.7 |
| 30 | 12.3 |
| 40 | 15.5 |
| 50 | 18.4 |

Figure 3:
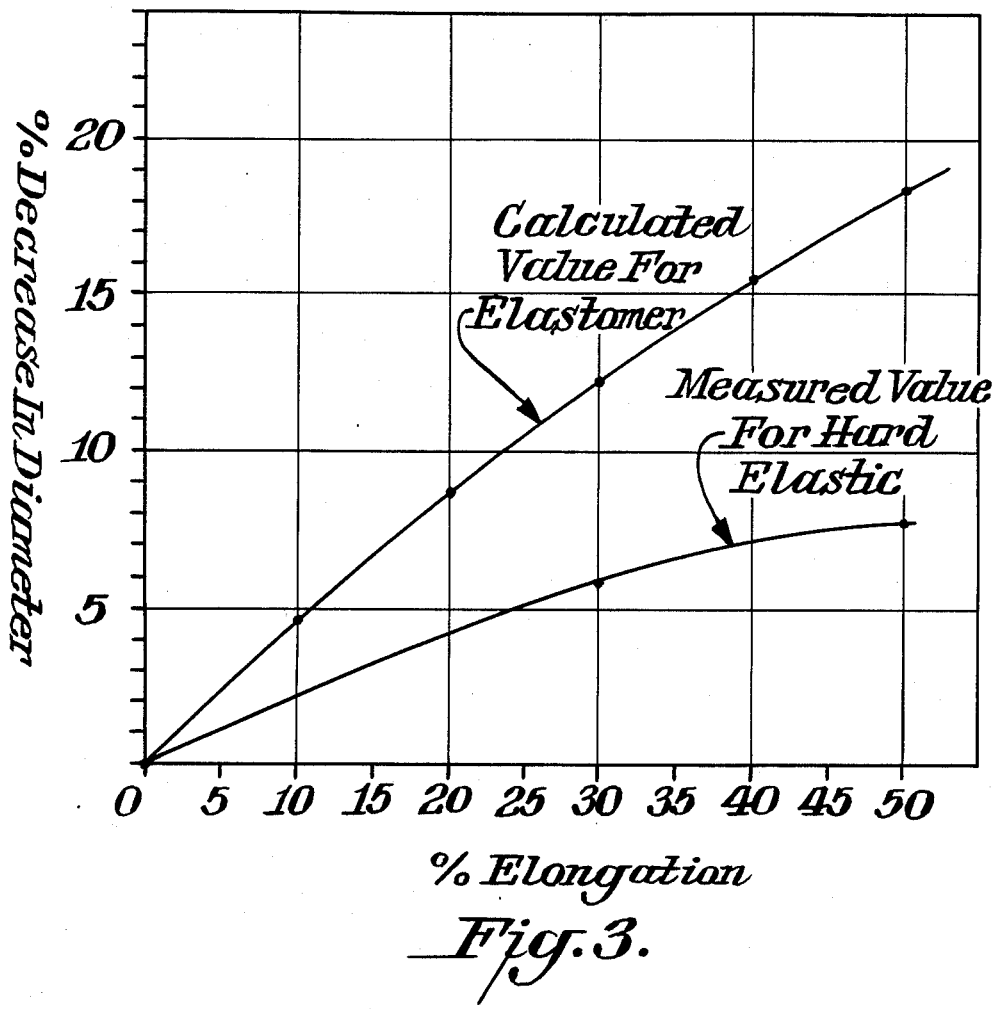
FIG. 3 presents curves comparing the % decrease in diameter vs. % elongation of a conventional elastomeric filament with a hard elastic filament of the invention.

The measured decrease in diameter for a hard elastic polypropylene filament of size 9-0 (0.036 mm) of the invention is set out in FIG. 3. As shown in FIG. 3, the measured decrease in diameter of the hard elastic filament is substantially less than the calculated diameter decrease of the conventional elastomeric filament. Generally, the % diameter decrease of a hard-elastic filament of the invention ranges from 0 to 10% on 50% stretching, and from 0 to about 8% in the case of the hard elastic filament of FIG. 3.

According to one embodiment of the invention, the hard elastic filament shows little or no decrease in diameter on stretching, e.g. about 3 to 4% diameter decrease on stretching to 25%, 30% or 50% of the original length.

According to a preferred embodiment of the invention, on 100% extension the filament has at least about 80% instantaneous recovery and 10% remaining recovery within a few minutes.

Generally, a monofilament suture having a Young's modulus of about 0.25 g/d to about 5.0 g/d is suitable for use in the invention, although this range is not critical to the invention. When softer hard elastic filaments are desired, the filament may be subjected to a final heat treatment step while the filament is in a stretched condition. For example, H. D. Noether et al., Textile Res. J., 46, 467-478 (1976) report production of hard elastic filaments with much reduced Young's modulus by heat treatment at 130° C. and 100% extension for 30 minutes. Materials of high elasticity in the 1-10 g/d modulus range and having tenacities between 1 and 4 g/d are formed.

The invention is not limited to hard elastic filaments made by any particular method. In general, hard elastic filaments may be produced from suitably crystalline polymers by spinning under high stress conditions as known to those skilled in the art. The high stress spinning conditions, particularly the melt temperature and draw ratio, depend on the particular polymer material being used. For instance, polybutene-1 generally requires spinning at melt temperatures of about 190° to 300° C. and at draw ratios of about 10 to about 5,000, preferably 100 to 400. Polybutylene oxide requires a melt temperature of from about 175° C. up to the decomposition temperature of polybutylene oxide and a draw ratio of about 50 to 1000, preferably 300 to 500. Polypropylene requires generally a melt temperature of about 160° to 260° C. and draw ratios of about 60 to 300. Temperatures of above about 60° C. and above about 100° C. are used for polyamides and polyesters, respectively, with draw ratios of about 200 to 4,000.

After suitable hard elastic filaments have been produced, they must be converted into sutures. If the suture is not to be a monofilament, a plurality of filaments may be combined, as by braiding, into a multifilament braid. The monofilament or multifilament strand is cut into desired lengths and sterilized. Needles may be attached. The sutures, with or without needles, are packaged in sterile enclosures to maintain sterility until time of use. Alternatively, sterilization may take place after packaging. Methods for carrying out these conversion steps are well known in the art, and the invention is not limited to any particular combination of them.

Monofilament hard elastic sutures in 9-0 (0.030–0.39 mm in diameter) and 10-0 (0.020–0.029 mm in diameter) size are especially useful for ophthalmic surgery. However, both mono- and multifilament hard elastic sutures can be made in a wide range of sizes suitable for many surgical procedures. The unusual elastic properties of the sutures of the invention will be beneficial to surgery requiring difficult anastomosis such as bowel and blood vessel anastomosis, and microsurgery to reconnect nerves. The sutures of the invention are also uniquely suitable in plastic and reconstructive surgery generally using a size range of about 4-0 (0.15–0.199 mm in diameter) to 7-0 (0.05–0.069 mm in diameter), and preferably 5-0 (0.10–0.149 mm in diameter). Also, sutures according to this invention can be made of any body-compatible polymer that can be sterilized, has the required strength and can exhibit the property of hard elasticity. The sutures of the invention can be dyed with dyes conventionally utilized in corneal surgery such as copper phthalocyanine.

The following example illustrates the invention.

EXAMPLE

Polybutylene (Shell Polybutylene 4110) was melt-spun into a multifilament yarn at a spin draw ration of 126. Table 1 sets out the physical properties of the polybutylene (PB) used. Individual filaments in the yarn measured 0.076 mm. in diameter. A hard elastic PB filament was formed having a stress-strain curve and a cyclic load-strain hysteresis curve characteristic of hard elastic filaments as shown in FIGS. 1 and 2.

Figure 1:
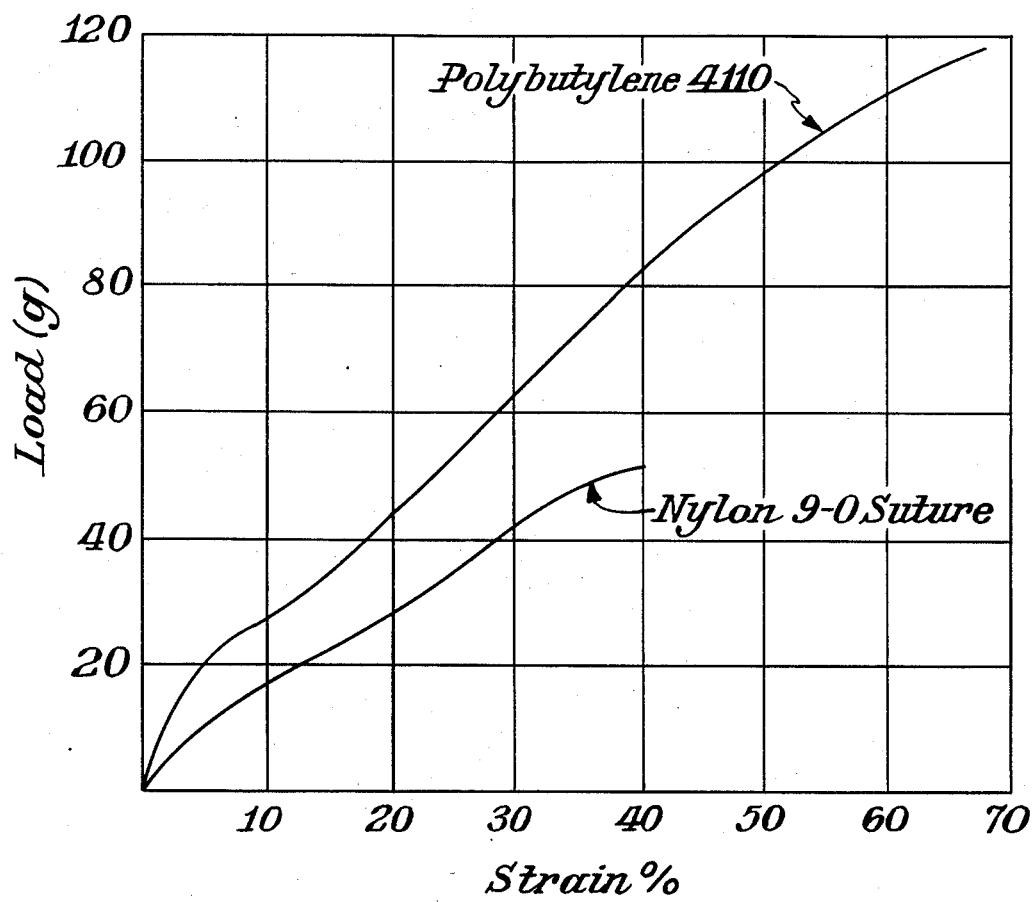
FIG. 1 presents stress-strain curves of a nylon 9-0 suture (0.036 mm. diameter) and a polybutylene filament according to the invention.
Figure 2:
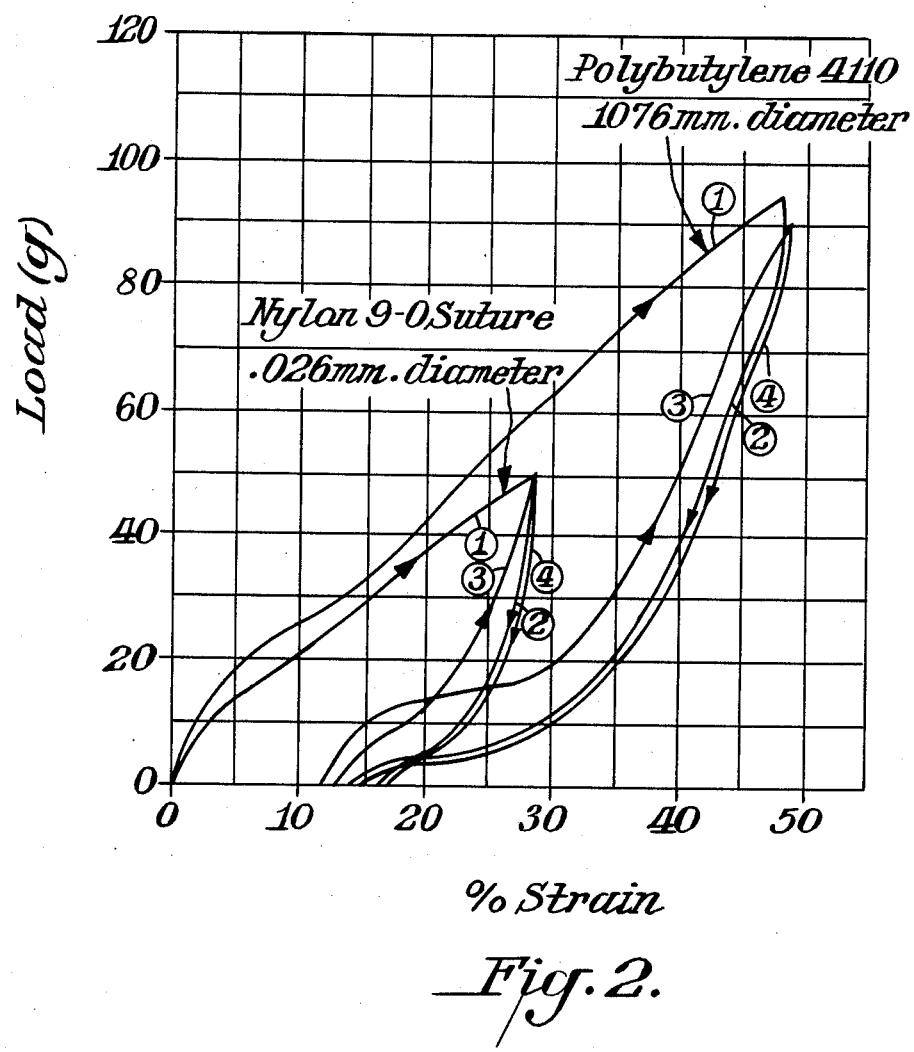
FIG. 2 presents hysteresis curves of the nylon suture and the polybutylene filament.

The change in the slope of the curve for the PB filament at about 6% strain in FIG. 1 does not represent a yield point where deformation is irreversible. The PB filament broke at about 68% strain and showed good recovery up to 50% strain.

The curve for the nylon suture in FIG. 1 has two yield points at about 4% and about 35% strain. The nylon suture thus has two yield points before 50% strain whereas the PB filament has none. The nylon suture broke at 50% strain and showed no recovery after 35% strain.

The initial elastic recovery ratio of the PB filament after one elongation (1) to 50% of the original length and relaxation (2) was about 75%. FIG. 2 also presents the hysteresis curve on second elongation (3) and relaxation (4). Recovery ratios increased to about 96% after elimination of residual set in the first elongation relaxation cycle. The final reversible elongation was at least 30% with 96% recovery.

FIG. 2 shows the hysteresis curves of the nylon suture after one elongation (1) relaxation (2) cycle and a second elongation (3) relaxation (4) cycle. The nylon suture has 60% elastic recovery after the first cycle to 30% strain, and 78% elastic recovery on subsequent cycles. The final reversible elongation was only 15% with 78% recovery.

TABLE 1

| | ASTM Test Method | English | | Metric | |
|---|---|---|---|---|---|
| | | Unit | Value | Unit | Value |
| General properties | | | | | |
| Melt index | D 1238 | — | — | g/10 min | 0.4 |
| Density | D 1505 | lb/ft$^3$ | 57.1 | g/cm$^3$ | 0.915 |
| Mechanical properties | | | | | |
| Tensile strength at yield | D 638 | psi | 2400 | kg/cm$^2$ | 170 |
| Tensile strength at break | D 638 | psi | 4800 | kg/cm$^2$ | 340 |
| Elongation at break | D 638 | % | 280 | % | 280 |
| Modulus of elasticity | D 638 | psi | 38,000 | kg/cm$^2$ | 2700 |
| Thermal Properties | | | | | |
| Melting point range | DTA | °F. | 225–259 | °C. | 124–126 |
| Softening point vicat | D 1525 | °F. | 235 | °C. | 113 |

I claim:

1. A surgical suture comprising at least one sterile hard elastic filament of a body-compatible polymer.

2. A surgical suture as in claim 1 wherein the suture is a monofilament.

3. A surgical suture as in claim 2 wherein the polymer is selected from the group consisting of polypropylene, poly(butene-1), ethylene-butylene copolymer, nylon and polyester.

4. A surgical suture as in claim 3 wherein the monofilament is 0.020–0.039 mm in diameter.

5. A surgical suture as in claim 2 wherein the monofilament is 0.05–0.199 mm in diameter.

6. A surgical suture as in claim 2 wherein the polymer is polypropylene or poly(butene-1) and the Young's modulus of the filament is 0.25–5.0 g/denier.

7. A surgical suture as in claim 1 wherein the suture is a multifilament suture.

8. A surgical suture as in claim 7 wherein the polymer is selected from the group consisting of polypropylene, poly(butene-1), ethylene-butylene copolymer, nylon and polyester.

9. A surgical suture as in claim 8 wherein the multifilament suture is a braided suture.

10. A surgical suture as in claim 1 wherein the polymer is a body-absorbable polymer.

11. A surgical suture as in claim 10 wherein the polymer is selcted from the group consisting of polyhydroxybutyric acid, polyglycolic acid and polylactic acid.

12. A needled surgical suture comprising at least one sterile hard elastic filament of a body-compatible polymer attached to a sterile surgical needle.

13. A needled surgical suture as in claim 12 wherein the polymer is polypropylene or poly(butene-1).

14. A surgical suture package comprising a sterile enclosure containing a sterile needled surgical suture, the suture comprising at least one hard elastic filament of a body-compatible polymer.

15. A surgical suture package as in claim 14 wherein the polymer is polypropylene or poly(butene-1).

16. A method of suturing by stitching with at least one sterile hard elastic filament made of a body-compatible polymer.

17. A method as in claim 16 wherein the polymer is selected from the group consisting of polypropylene, poly(butene-1), ethylene-butylene copolymer, nylon and polyester.

18. A method as in claim 17 wherein the polymer is polypropylene and the filament is 0.020–0.039 mm. in diameter.

19. A method as in claim 17 wherein the filament has a Young's modlus of 0.25–5.0 g/denier.

20. A method as in claim 16 wherein said stitching is performed in corneal surgery.

* * * * *